(12) United States Patent
Forcella et al.

(10) Patent No.: US 9,835,533 B2
(45) Date of Patent: Dec. 5, 2017

(54) TABLET TESTING DEVICE

(71) Applicant: PHARMATRON AG, Thun (CH)

(72) Inventors: Bruno Forcella, Steffisburg (CH); Francois Junod, Jegenstorf (CH)

(73) Assignee: Sotax AG, Aesch BL (CH)

( * ) Notice: Subject to any disclaimer, the term of this patent is extended or adjusted under 35 U.S.C. 154(b) by 242 days.

(21) Appl. No.: 14/344,063

(22) PCT Filed: Oct. 19, 2012

(86) PCT No.: PCT/IB2012/055735
§ 371 (c)(1),
(2) Date: Apr. 25, 2014

(87) PCT Pub. No.: WO2013/061223
PCT Pub. Date: May 2, 2013

(65) Prior Publication Data
US 2015/0033869 A1 Feb. 5, 2015

Related U.S. Application Data

(60) Provisional application No. 61/550,951, filed on Oct. 25, 2011.

(30) Foreign Application Priority Data

Oct. 25, 2011 (EP) .................... 11186470

(51) Int. Cl.
*G01N 3/08* (2006.01)
*G01B 5/00* (2006.01)
*G01N 33/15* (2006.01)

(52) U.S. Cl.
CPC ............ *G01N 3/08* (2013.01); *G01B 5/00* (2013.01); *G01N 33/15* (2013.01); *G01N 2203/0019* (2013.01); *G01N 2203/0087* (2013.01)

(58) Field of Classification Search
CPC .................................................. G01N 3/08
(Continued)

(56) References Cited

U.S. PATENT DOCUMENTS 1,857,808 A 5/1932 Diederichs
4,219,986 A 9/1980 Osterhaus
(Continued)

FOREIGN PATENT DOCUMENTS

CA 2428801 A1 11/2003
CA 2526758 A1 5/2006
(Continued)

OTHER PUBLICATIONS

International Search Report and International Preliminary Report on Patentability, dated May 6, 2014, from parent PCT/IB2012/055735; in English.
(Continued)

*Primary Examiner* — Lisa Caputo
*Assistant Examiner* — Octavia Hollington
(74) *Attorney, Agent, or Firm* — Nadya Reingand; Yan Hankin

(57) ABSTRACT

The invention relates to a tablet testing device for testing tablets with at least one tablet testing station suitable for carrying out at least one test procedure, and preferably at least one apparatus suitable for receiving, and possibly also crushing, the tablet, and also at least one device for positioning a test specimen in accordance with the procedure. The device in accordance with the invention for positioning the tablet includes at least one movable positioning surface, preferably a flap, and at least one further surface that interacts with this positioning surface for the purpose of positioning the tablet.

11 Claims, 5 Drawing Sheets

Figure 1:
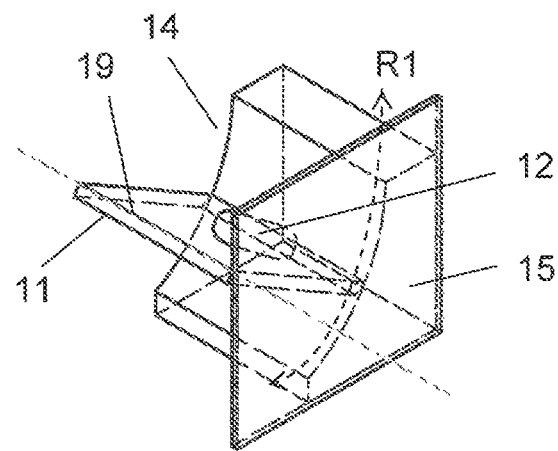

(58) Field of Classification Search
USPC .................................. 73/821; 198/464.2
See application file for complete search history.

(56) References Cited

U.S. PATENT DOCUMENTS

| | | | |
|---|---|---|---|
| 4,393,717 | A | 7/1983 | Mason et al. |
| 4,434,887 | A | 3/1984 | Yager |
| 4,472,960 | A | 9/1984 | Motoyama et al. |
| 4,542,646 | A | 9/1985 | Smith et al. |
| 4,546,901 | A | 10/1985 | Buttarazzi |
| 4,660,713 | A | 4/1987 | Kaminski |
| 4,784,275 | A | 11/1988 | Fridge |
| 4,907,790 | A | 3/1990 | Sugiura et al. |
| 4,930,289 | A | 6/1990 | Fransson et al. |
| 5,012,913 | A | 5/1991 | Kraemer |
| 5,190,162 | A | 3/1993 | Hartlepp |
| 5,240,118 | A | 8/1993 | Mayer |
| 5,466,290 | A | 11/1995 | Berta |
| 5,503,673 | A | 4/1996 | Berta |
| 5,522,512 | A | 6/1996 | Archer et al. |
| 5,555,768 | A | 9/1996 | Shaffer et al. |
| 5,638,417 | A | 6/1997 | Boyer et al. |
| 5,679,406 | A | 10/1997 | Berta |
| 5,971,038 | A | 10/1999 | Fiedler et al. |
| 6,237,743 | B1 | 5/2001 | Bracher |
| 6,257,079 | B1 * | 7/2001 | Mueller ............... G01G 17/00 177/50 |
| 6,260,419 | B1 | 7/2001 | Kraemer |
| 6,820,498 | B2 | 11/2004 | Kalbermattern |
| 7,364,103 | B2 | 4/2008 | Kraemer et al. |
| 9,389,213 | B2 * | 7/2016 | Boss ................... G01N 3/40 |
| 2003/0209098 | A1 | 11/2003 | Kalbermattern |
| 2004/0144618 | A1 | 6/2004 | McDonald et al. |
| 2005/0103132 | A1 | 5/2005 | Bracher et al. |
| 2005/0263537 | A1 | 12/2005 | Gerold et al. |
| 2006/0260413 | A1 | 11/2006 | Kraemer et al. |
| 2008/0105516 | A1 | 5/2008 | Richwine |

FOREIGN PATENT DOCUMENTS

| | | |
|---|---|---|
| DE | 8911221 U1 | 11/1989 |
| DE | 4241985 A1 | 6/1994 |
| DE | 19744227 A1 | 11/1998 |
| DE | 102004036777 A1 | 3/2006 |
| DE | 102004059976 A1 | 6/2006 |
| DE | 202008003673 U1 | 5/2008 |
| DE | 102007056244 A1 | 5/2009 |
| DE | 102008035830 A1 | 2/2010 |
| DE | 102010012198 A1 | 9/2011 |
| EP | 0685714 A1 | 12/1995 |
| EP | 1361418 A1 | 11/2003 |
| EP | 1531317 A1 | 5/2005 |
| FR | 2142655 A | 2/1973 |
| FR | 2933079 A1 | 1/2010 |
| GB | 728097 A | 4/1955 |
| GB | 728111 A | 4/1955 |
| GB | 871685 A | 6/1961 |
| GB | 1032417 A | 6/1966 |
| GB | 1288584 A | 9/1972 |
| GB | 2214500 A | 9/1989 |
| JP | S61-084556 A | 4/1986 |
| JP | S61-127519 A | 6/1986 |
| JP | S62-295432 A | 12/1987 |
| JP | H02-099862 A | 4/1990 |
| JP | H02-255149 A | 10/1990 |
| JP | H05-079964 A | 3/1993 |
| JP | H05-079966 A | 3/1993 |
| JP | S63-076863 A | 4/1998 |
| JP | H10-160554 A | 6/1998 |
| JP | 2001-095897 A | 4/2001 |
| JP | 2003-347330 A | 12/2003 |
| WO | 2009/038380 A2 | 3/2009 |
| WO | 2011/035818 A1 | 3/2011 |
| WO | 2013/061223 A3 | 6/2014 |

OTHER PUBLICATIONS

International Search Report, dated Feb. 7, 2014, from parent PCT/IB2012/055735; in English.
European Search Report of EPO in priority Application No. EP11186470, dated Feb. 14, 2012.
Copending commonly owned U.S. Appl. No. 14/344,066.

* cited by examiner

TABLET TESTING DEVICE

This application is a 35 U.S.C. 371 national-phase entry of PCT International application no. PCT/IB2012/055735 filed on Oct. 19, 2012 and also claims benefit of priority to prior European application no. EP11186470 filed on Oct. 25, 2011, and also claims priority as a non-provisional of U.S. provisional application Ser. No. 61/550,951 filed on Oct. 25, 2011, and both European application no. EP11186470 and U.S. provisional application Ser. No. 61/550,951, as well as parent PCT International application no. PCT/IB2012/055735, are all incorporated herein by reference in their entireties for all intents and purposes, as if identically set forth in full herein.

The invention relates to tablet testing devices for testing tablets, as well as to methods of testing tablets in said tablet testing devices.

Such tablet testing devices are used in research and industry in order to meet the very high quality requirements, above all in the pharmaceutical sector. These devices are manually operated, semi- or fully automatic. They measure, for example, the weight, thickness, diameter, length and width as well as the hardness, that is, the breaking strength and breaking behaviour of tablets, using mechanical, electronic, optical, chemical or acoustic methods. As tablets come in a wide variety of shapes, the optimum and secure positioning of a tablet relative to a measuring device in the relevant method poses a great challenge the developers and users of such tablet testing devices, particularly if, on one tablet testing station, various test procedures are implemented that require different positioning of the tablet.

From DE 102004036777A1 a device for testing the breaking strength of oblong tablets with a horizontal transporting belt is known. It has a stationary breaking surface acting as a stop for oblong tablets on one side of the transporting belt, and on the other side of the transport belt, another breaking surface that is movable and is connected to an actuating and measuring device. It aligns the oblong tablets by two adjacently arranged rollers rotating in opposite directions.

On the one hand, a drawback of this known solution is the relatively elaborate, space-consuming and maintenance-intensive design with two separate motors and the roller as such, and, on the other hand, the fact that, particularly for small tablets and tablets of certain shapes, this tablet testing device cannot be used.

Known from DE 102008035830A1 is a tablet testing device for carrying out a hardness test, and length, width and height measurement of test specimens. It includes a pressure measuring container, a pressure plate, a stop and a laser measuring device, in which the stop, push bars connected to a pusher and a shaft for moving guide clamps are arranged on a base plate. Guide clamps are described to have depression-like openings with a recess for receiving and positioning a tablet, as well as a measuring space. Provided on the base plate is a table surface for the tablet which can be moved in the direction of the stop. A pressure measuring sensor is connected to the slide and the pressure plate.

This solution is not only complex and expensive like the solution in DE 102004036777A1, but is not suitable for all conceivable forms of tablet, nor for all forms of feeding-in of the tablets.

From the DE 102004059976A1 a further device with a testing station for testing the breaking strength of tablets is known, comprising several measuring stations for carrying out various testing methods on a tablet. A tablet is introduced into a breaking strength measurement station by means of a transport rake. In the transporting direction of the transport rake behind the breaking strength measurement station a pivotable abutment flap is provided for receiving the tablet in the breaking strength measurement station. After the breaking strength measurement, the abutment flap is pivoted away and the broken tablet is pushed out of the measurement station.

With this solution the clearances in the transport rake determine the orientation of the tablet, which cannot be turned from one orientation into another. Moreover, this solution requires that the dimensions of the tablet be known, rendering this tablet testing device only feasible for certain tablets.

From the DE 202008003673U1 a device for orientating of objects, in particular tablets, for the purpose of carrying out measurements is known. A turnable roll and a flap pivotable with respect to this roll are provided as supporting points for the tablet. The orientation of the tablet is achieved by the turnable roll.

The complex arrangement of this solution is a great disadvantage, since two separate drives have to be provided for roll and flap. These drives must be controllable independently from each other. In addition, the gap between the roll and the flap determines the minimal size the tablet must have, and this narrows the range of use of this device.

The object of the invention is therefore to make available a tablet testing device for the testing of tablets which overcomes the aforesaid disadvantages, that is, being smaller, cheaper, simpler and, in particular being usable for tablets of every shape in different test procedures and in different test equipment. A further object of the present invention is a method for the testing of tablets with such tablet testing device achieving the same advantages.

The first object may be achieved through some of the disclosed features, and the further object may be achieved though some of the disclosed features. Advantageous further embodiments are set out in the figures and in the disclosure.

In accordance with the invention, the design of the means for positioning tablets in the form of two interacting surfaces, with at least one of them being pivotable, is associated with great economic and technical improvements: this relatively simple design is cost-effective and maintenance-friendly. The further surface may be a curved positioning surface formed along the radius of the pivoting movement of the first surface, may be a further positioning surface moving together with the first surface and protruding in a defined angle from it, or may be a further positioning surface on a further flap which is pivotable and/or can be displaced in the planar direction. This allows process-adapted positioning of every conceivable elongated tablet within the shortest time and is, in principle, imaginable within every testing process and with every manner of manual or automatic feeding.

For the sake of simplicity, but certainly not restricted to these processing stages, the arrangement, in accordance with the invention, of a tablet testing device in a tablet testing station that tests the length, width and hardness, that is, the breaking strength or breaking behavior, shall be described. In such a tablet testing station advantages according to the invention become clearest to a person skilled in the art, as different positioning of the tablets during the various processing stages with tablet testing devices from the prior art is not achieved adequately, or is achievable only with considerable effort. Above all, it is difficult to reposition the tablet before and between the measuring procedures for preparing the breaking strength test, during which the tablet is usually destroyed. If the tablet is not brought into the correct position for each measuring or testing procedure, often due to is special shape, the measuring or test result is inadequate.

The tablet is manually or preferably automatically supplied to the tablet testing station in accordance with the invention, and lands on a random point on a movable positioning plane, preferably designed as a type of flap. Though a movement of the positioning plane is it initially brought into the ideal position for measurement of the length and width. After measurement, the tablet is newly orientated through a pivoting movement of the positioning plane, as, irrespective of how it was lying before, for the hardness test it must be brought into precise alignment between two pressures surfaces, at least one of which is generally provided with the measuring device which implements the hardness test. For this test procedure a longitudinal orientation of the tablet is normally required. Finally, the tablet, either intact or broken, is removed from the testing process.

In one embodiment in accordance with the invention the surface which interacts with the movable positioning surface, preferably flap, in order to orientate the tablet, is designed as a second flap which is in parallel to and pivotable against the first flap, and preferably, in order to have the same positioning effect as the flap which is only pivotable, is arranged to move longitudinally relation thereto. With an embodiment of this type it is also possible to realign tablets, even those with a position varying greatly from the ideal position. However the embodiment with two flaps has the design and therefore economic disadvantage that is requires two separate motors. A procedural drawback is that a tablet can unintentionally become stuck between the two surfaces. Also it is easily possible to lose the tablet to the waste bin before completion of all measuring procedures if it unintentionally slips between the two flaps as a result of an unfortunate positioning angle. The economically preferred solution is therefore the one with one flap.

The invention shall be described in more detail below symbolically and exemplarily with the aid of the figures. The figures are described in summary and overall. The same reference numbers denote the same components throughout. The list of reference numbers also forms part of the disclosure.

Figure 2:
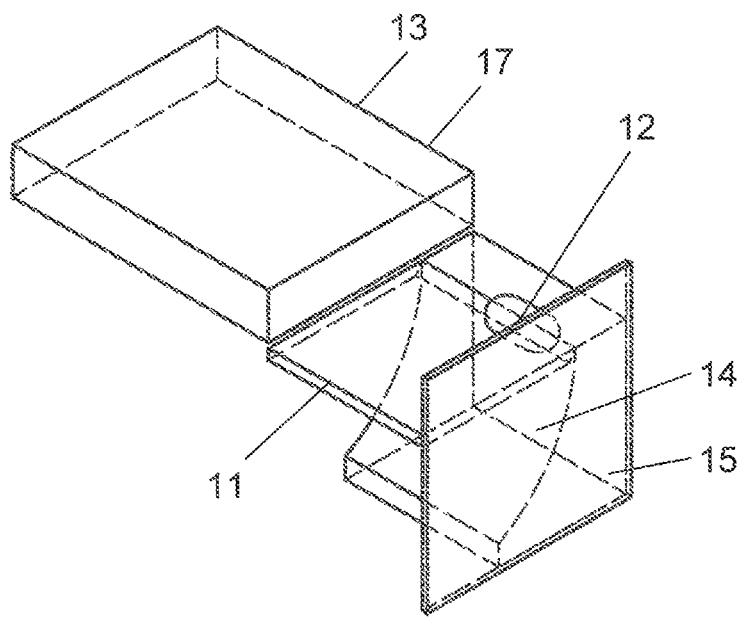
Figure 3:
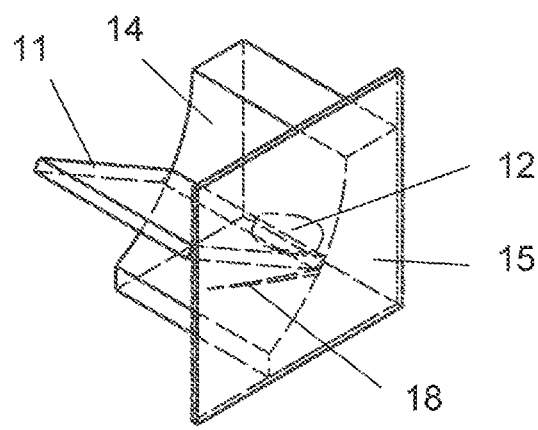
Figure 4:
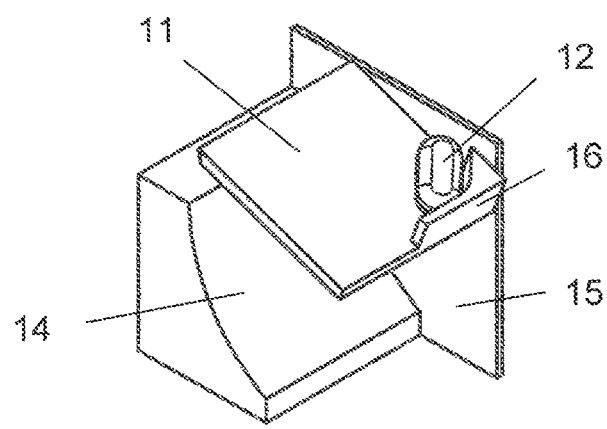
Figure 5:
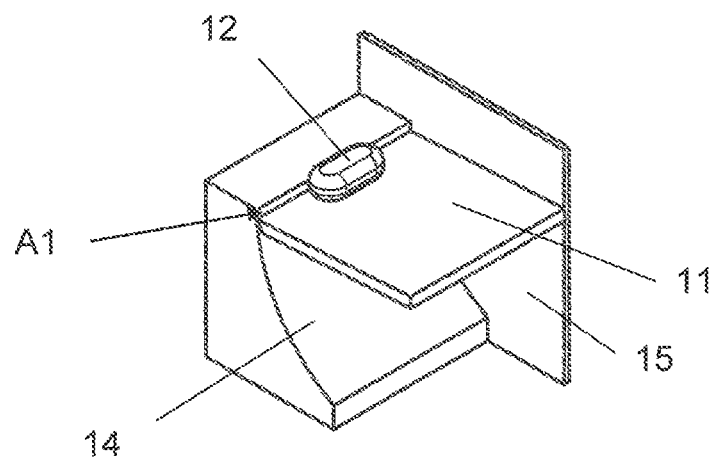
Figure 6:
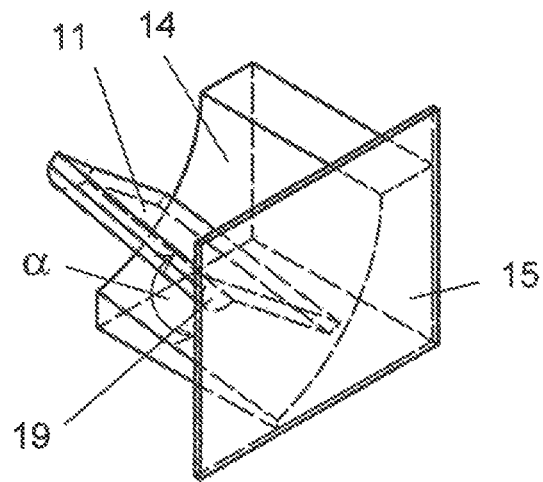
Figure 7:
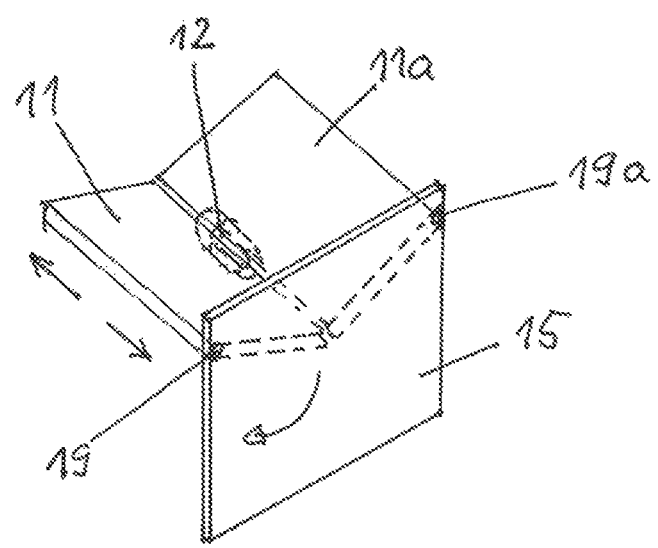
Figure 8A:
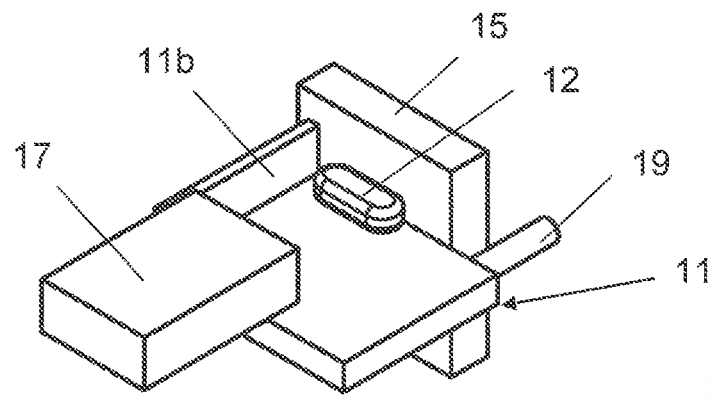
Figure 8B:
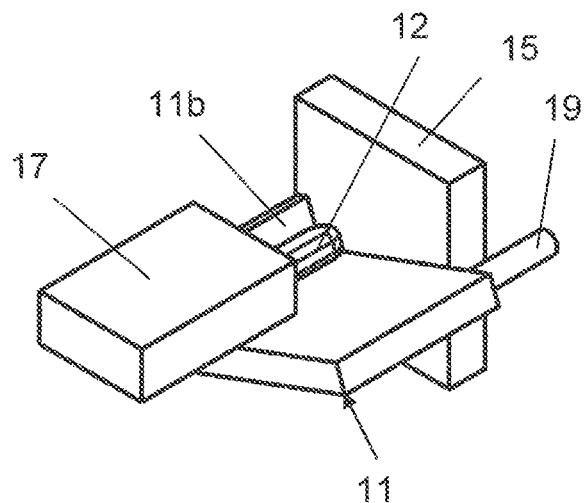
Figure 9:
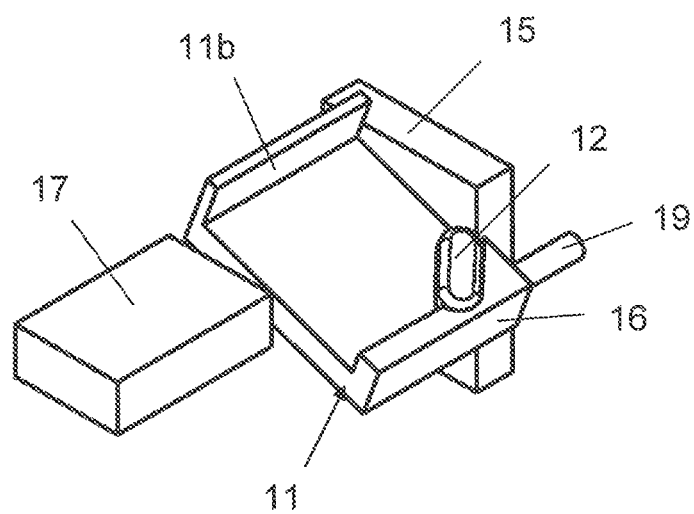
Figure 10:
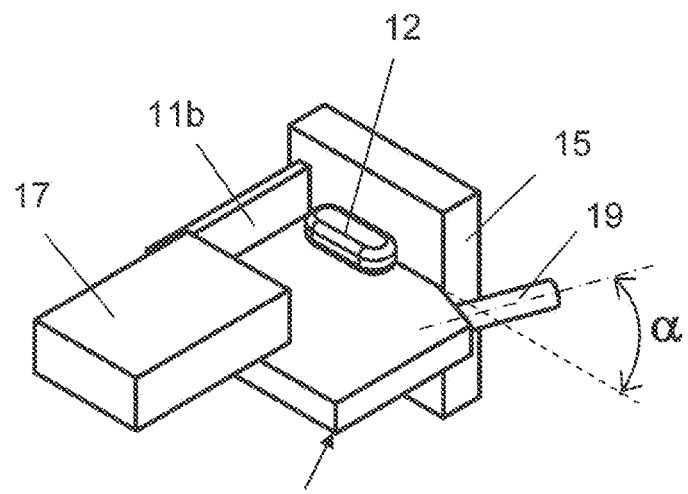
Figure 11:
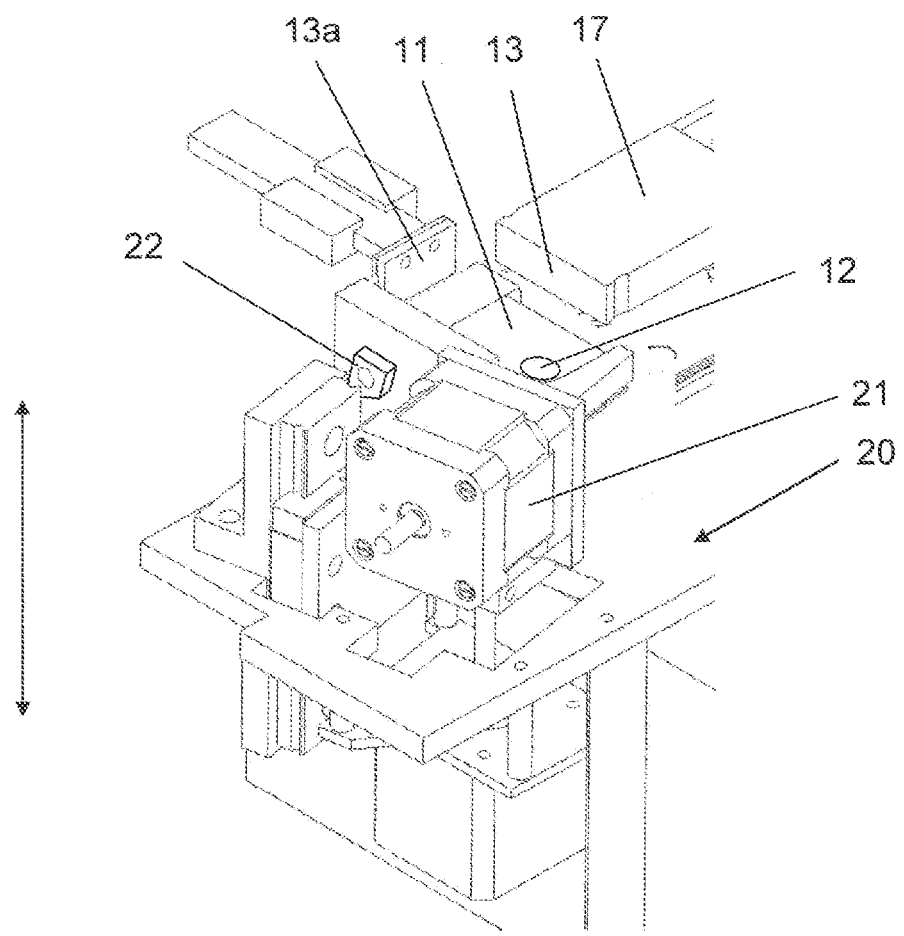

In the drawings:

FIG. 1—shows a schematic view of a first example of embodiment of a tablet testing device in accordance with the invention, FIG. 2—shows a schematic view of an example of a tablet testing device in accordance with the invention with a breaking surface/a measuring device, FIG. 3—shows a schematic view of an example of embodiment of a tablet testing device with an interference contour on the positioning surface, FIG. 4—shows a schematic view of an example of embodiment of a tablet testing device in accordance with the invention with a redirecting element on the positioning surface, FIG. 5—shows a schematic view of an example of embodiment of a tablet testing device in accordance with the invention with a slightly lowered positioning surface, FIG. 6—shows a schematic view of an example of embodiment of a tablet testing device in accordance with the invention with an angled positioning surface, FIG. 7—shows a schematic view of an example of embodiment of a tablet testing device in accordance with the invention with two flaps that are pivotable and movable on the planar direction, FIG. 8a—shows a schematic view of an example of embodiment of a tablet testing device with an additional positioning surface protruding from the movable flap and pivoting together with said flap, with the flap in horizontal position, FIG. 8b—shows a schematic view of the embodiment of FIG. 8a with the flap pivoted below the horizontal position, FIG. 9—shows a schematic view of an example of embodiment of a tablet testing device with an additional positioning surface protruding from the movable flap and having a redirecting or interference contour, FIG. 10—shows a schematic view of an example of embodiment of a tablet testing device with a pivoting axis being oblique with respect to the further positioning surface pivoting together with the flap, and, FIG. 11—shows schematic view of an example of embodiment of a tablet testing device in accordance with the invention with a lift.

The arrangement set out in FIG. 1 depicts part of a testing station of a table testing device with relevance to the invention. Here, a tablet 12 lies on a first positioning surface, designed as a flap 11, that is shown pivoted relative to a second positioning surface shown here as curved surface 14. The curved surface 14 is provided along the rotation line (arc) R1 of the outer edge of the flap 11 facing it so that the predetermined, preferably as small a gap as possible, between the two remains the same during the pivoting movement of the flap 11. Perpendicularly to the axis of rotation 19 of the flap and to the curved surface 14 a further positioning surface is to be imagined, which in this case is designed as a fixed breaking surface 15 and may also interact with the flap 11 and/or with the curved surface 14 in order to position the tablet 12. It may be designed, for example, as a mounting for a rotation axle 19, preferably in the form of a rotating shaft, or as a wall of the actuator driving the rotating shaft. In each case, during a testing procedure the tablet 12 is pushed by a movable breaking surface 17 (shown in FIG. 2) against this fixed breaking surface 15.

FIG. 1 depicts how when the flap 11 is pivoted, the tablet 12, obeying the laws of gravity, slides down towards the curved surface 14 and comes to rest against it, in a manner dependent on its own weight and on the pivoting movement. The rotation movement of the flap 11 is adapted to the shape of the tablet 12 and to the required end position. It may range from simple vibration to a large pivoting movement to below the curved surface 14, the latter pivoting movement removing the test specimen from the tablet testing station.

In principle FIG. 2 depicts the same arrangement as in FIG. 1, but with one breaking surface 17 as the positioning surface, which can preferably be moved over the shown arrangement. For testing purposes it pushes the test specimen 12 located on the flap 11 up to the fixed breaking surface 15, where the actual pressure test takes place. The tablet 12 is pressed by the breaking surface 17 against the fixed breaking surface 15 at a predefined force, or a predefined time, or until it breaks. The breaking surface 17 then returns to its initial position shown in FIG. 2 and the flap it pivoted downwards until the tablet 12, either intact or broken, falls out of the tablet testing station through gravitational force.

FIG. 3 depicts a variant of the arrangement in FIG. 1. On the curved surface 14 there is an interference contour 18, that is, the curved surface 14 is not designed exactly along the line of rotation (arc) R1 of the facing outer edge of the flap 11, but has a ridge or recess there so that the predetermined, preferably as small a gap as possible between the two, may vary during the pivoting movement of the flap 11;

or so that a tablet 12 sliding along the curved surface 14 is subject to increased sliding resistance. As a result of this, on the one hand the desired lateral displacement or tilting of the tablet depicts be brought about, or, on the other hand, through its special design of the curved surface 14 the result may be achieved that the rotational movement of the flap 11 and/or sliding movement of the tablet 12 is not linear, but is interrupted. Through interrupting the pivoting and/or sliding movement, a slight vibration of the flap 11 and/or the tablet is produced and in turn brings about a repositioning of the tablet 12.

FIG. 4 depicts a preferred embodiment of the flap 11 also with a redirecting element 16 similar to an interference contour. Here, when the flap 11 is pivoted upwards, whereby the outer edge preferably projects over the curved surface 14, the tablet is initially pressed against the redirecting element 16 through gravity, as shown in FIG. 4, in order when the flap 11 is then pivoted downwards to then also be positioned through gravity in the required parallel position against the curved surface.

FIG. 5 depicts how, after alignment of the tablet (FIGS. 1-4) the flap is not moved completely upwards into a horizontal position in order to produce a lateral guide A1 for the tablet through the curved surface 15. In this way turning of the tablet may be prevented for the subsequent test procedure.

FIG. 6 also depicts a preferred embodiment of the arrangement in accordance with the invention. Here the axis of rotation 19 of the flap 11, preferably in the form of a rotating shaft, is pivotable. The curved surface 14 is designed accordingly along the changed line of rotation. In this way the rotation axis 19 of the flap 11 may be angled so that again through the force of gravity the tablet 12 is forced into a required position through the oblique positioning of the flap 11 in relation to the curved surface 14. It is possible to predefine the angle α of rotation axis 19/fixed breaking surface 15 in accordance with the shape and the weight of the tablet. A desirable tablet position in most cases is as close to the fixed breaking surface as possible, whereby subsequent, time-consuming and positioning-endangering movement by the moveable breaking surface is dispensed with, and the testing procedure may take place immediately.

FIG. 7 depicts an arrangement in accordance with the invention with a flap 11 and a further positioning surface, here in the form of flap 11a which are arranged in parallel to each other and pivot in relation to each other in a known manner. In a preferred embodiment its two actuators (not visible here) are newly designed so that the flaps 11 and 11a are not only pivotable, but may also be moved on the planar direction, that is, along the axis of rotation 19 and 19a, respectively. In this way, the two flaps 11 and 11a may be displaced with regard to each other. Through gravity the position of the tablet may be changed through each of the two movements of the positioning surfaces. If both flaps 11 and 11a are pivoted downward until they form a V-shape with regard to each other, the tablet 12 undergoes longitudinal orientation in relation to the two breaking surfaces 15 and 17 (which is not shown here), i.e. the movable breaking surface. If the flaps 11 and 11a are in the same plane and longitudinally displaced with regard to each other by any suitable displacement mechanism, due to gravity the tablet is transversely orientated via the friction, in other words it is positioned in parallel to the breaking surfaces 15 and 17.

FIGS. 8a and 8b depict schematic views of a further example of the invention-relevant part of a tablet testing device according to the invention, in different positions. Again the tablet 12 lies on a first positioning surface, designed as a flap 11. On the edge of the flap 11 opposite the pivoting axis 19 a further and preferably plane positioning surface 11b is provided, which surface 11b moves together with the flap 11 and protrudes in a defined angle from the movable positioning surface of flap 11. Preferably the positioning surface 11b is integral with flap 11. The angle between the first positioning surface on flap 11 and the further positioning surface 11b is in a range between 45 and 135°, preferably 90°.

FIG. 8b depicts the situation when the movable flap 11 is pivoted downwards so that the tablet 12, obeying the laws of gravity, slides down towards the further positioning surface 11b and comes to rest against it depending on its own weight and the pivoting movement. The rotation movement of the flap 11 is adapted again to the shape of the tablet 12 and the required end position, as explained in detail in connection with FIG. 1. The movement of flap 11 may possibly be achieved by a vibration means 22, for example a vibration motor, as indicated schematically in FIG. 11.

FIG. 9 depicts an enhanced embodiment of a device according to FIGS. 8a and 8b. Again and similar to the embodiment of FIG. 4, a redirecting element 16 similar to an interference contour is provided on the side of flap 11 near the pivoting axis 19. In the shown position, with the flap 11 pivoted upwards, the tablet is initially pressed against the redirecting element 16 through gravity. Then, after the flap 11 is pivoted downwards the tablet 12 is directed into the required parallel position against the further positioning surface 11b on flap 11, again through gravity.

As can be gathered from FIG. 10, also with an embodiment as shown in FIGS. 8a and 8b, with a positioning surface 11b movable together with flap 11, the pivoting axis 19 of this flap 11 may preferably be pivotable or be fixed in an oblique angle with respect to a direction perpendicular to the fixed breaking surface 15. A pivoting axis 19 oriented like that brings flap 11 and further positioning surface 11b in a respective oblique position which forces the tablet 12 into the required position by the effect of gravity. Here again it is possible to predefine the angle α between the rotation axis 19 and the fixed breaking surface 15 in accordance with the shape and the weight of the tablet.

FIG. 11 depicts a preferred embodiment in accordance with the invention in which the further positioning surface, which interacts with the first positioning surface for the purpose of orientation, is designed as a height-adjustable unit, preferably a lift 20. This lift raises the entire device with the first movable positioning surface 11 or with the positioning surfaces 11 and 11a (not shown here) together with their actuator 21 upwards in order to acquire a tablet from a supply device (not shown). In accordance with the invention it moves as closely as possible to the supply device in order to prevent uncontrolled placing of the tablet on the flap 11. For the subsequent processing stages the lift descends in order, for example, to give the measuring devices 13, possibly integrated with the movable breaking surface 17, and 13a space. The lift shown here is described in more detail in a further application, which is to apply as an integral part of the present application.

The individual features described in connection with the figures may of course also be provided in other forms of embodiment or in combination with each other within the context of the claims.

LIST OF REFERENCE LABELS 11, 11a Flap/positioning surface
12 Tablet 13, 13a Measuring device
14 Curved surface
15 Fixed breaking surface/fixed surface
16 Redirecting element (interference contour)
17 Displaceable/movable breaking surface and/or further positioning surface
18 Interference contour
19, 19a Axis of rotation
20 Lift
21 Actuator
22 Vibration means
R1 Rotation line
α Angle of rotation axis 19/fixed breaking surface 15
A1 Guiding on curved surface

What is claimed is:

1. A tablet testing device comprising:
a tablet positioner;
at least one movable flap included in said tablet positioner, said flap being rotatable about an axis, said axis being located on said flap;
said at least one movable flap having a top surface;
said at least one movable flap having a bottom surface;
said at least one movable flap having an outer edge between its top and bottom surfaces; and,
a concavely curved tablet-positioning surface formed over an arcuate extent, said concavely curved tablet-positioning surface being located along an arc formed by said outer edge and being separated by a defined distance from said outer edge when said outer edge is pivoted along said concavely curved tablet-positioning surface,
said flap's positioning relative to said concavely curved tablet-positioning surface defining a movement of a tablet placed on said movable flap.

2. A tablet testing device as claimed in claim 1, further comprising:
an interference contour on said concavely curved positioning surface.

3. A tablet testing device as claimed in claim 2, further comprising:
said interference contour being formed by a ridge.

4. A tablet testing device as claimed in claim 2, further comprising:
said interference contour being formed by a recess.

5. A tablet testing device as claimed in claim 1, further comprising:
a tablet redirecting contour on said at least one movable flap.

6. The tablet testing device as claimed in claim 1, wherein:
said at least one movable flap is displaceable along an extent of said top surface.

7. A tablet testing device as claimed in claim 1, further comprising:
a vibration drive configured to vibrate said at least one movable flap.

8. A tablet testing device as claimed in claim 1, further comprising:
a fixed breaking surface; and,
said at least one movable flap having a rotation axis arranged at a predefined angle (α) to said fixed breaking surface.

9. A tablet testing device as claimed in claim 1, further comprising: a second moveable flap, said second moveable flap being in parallel to and pivotable against the at least one moveable flap, wherein a positioning of said flaps relative to each other defines a movement of a tablet placed on at least one of said movable flaps.

10. A tablet testing device as claimed in claim 1, wherein said defined distance is the same along an entirety of said outer edge.

11. A tablet testing device as claimed in claim 1, wherein a contour of said outer edge of said flap matches a contour of said concavely curved tablet-positioning surface.

* * * * *